United States Patent [19]
Takami et al.

[11] Patent Number: 4,825,683
[45] Date of Patent: May 2, 1989

[54] APPARATUS FOR EVALUATING AN OXYGEN SENSOR

[75] Inventors: Akio Takami, Konan; Ken Minoha, Tajimi; Mineji Nasu, Konan; Toshifumi Sekiya, Osaka; Toshitaka Matsuura, Komaki; Akio Mizutani, Nagoya; Noriaki Kondo, Ichinomiya, all of Japan

[73] Assignee: NGK Spark Plug Co., Ltd., Aichi, Japan

[21] Appl. No.: 139,295

[22] Filed: Dec. 29, 1987

[30] Foreign Application Priority Data

Dec. 29, 1986 [JP] Japan .................. 61-314357
Mar. 24, 1987 [JP] Japan .................. 62-69295

[51] Int. Cl.$^4$ ........................................... G01D 18/00
[52] U.S. Cl. ........................................... 73/1 G
[58] Field of Search .................................. 73/1 G

[56] References Cited

U.S. PATENT DOCUMENTS 4,094,186 6/1978 Wessel .................. 73/1 G
4,389,881 6/1983 Butler et al. ............ 73/1 G X
4,622,844 11/1986 Bienkowski ............. 73/1 G

FOREIGN PATENT DOCUMENTS 61-42224 9/1986 Japan.

OTHER PUBLICATIONS

S.A.E. Paper No. 790143, Title; Characteristics of $ZrO_2$—Type Oxygen Sensors for Automotive Applications; L. T. Young et al.; 1st 3 pages; 1979.

Primary Examiner—Tom Noland
Attorney, Agent, or Firm—Oliff & Berridge

[57] ABSTRACT

An apparatus for evaluating an oxygen sensor includes a device for mixing a fuel and an oxygen-containing gas in an appropriate ratio to prepare a fuel mixture. A burner is connected to the mixing device for burning the fuel mixture to produce a gaseous combustion product. A tubular member extends from the burner for supplying the combustion product. A nozzle is connected to the tubular member for introducing a fuel and an oxygen-containing gas into the tubular member so that the combustion product is of a desired excess air ratio (air-fuel ratio) and a mounting device for the sensor to be evaluated is disposed on the tubular member, downstream of the nozzle.

8 Claims, 10 Drawing Sheets

PRIOR ART

PRIOR ART

PRIOR ART

FIG. 11

PRIOR ART

PRIOR ART

FIG. 15

APPARATUS FOR EVALUATING AN OXYGEN SENSOR

BACKGROUND OF THE INVENTION

1. Field of the Invention

This invention relates to an apparatus for evaluating an oxygen sensor. More particularly, it is directed to an oxygen sensor evaluation apparatus which includes a burner.

2. Description of the Prior Art

There are several known types of apparatus for the evaluation of an oxygen sensor. They include the following:

(1) An apparatus in which the oxygen sensor to be evaluated contacts the exhaust gas of an engine;

(2) An apparatus in which the oxygen sensor to be evaluated contacts a model gas, such as a mixture of $H_2$, CO, HC, $O_2$ and $N_2$, for example, as disclosed in Japanese Patent Publication No. 42224/1986.

(3) An apparatus in which the oxygen sensor to be evaluated contacts the combustion gaseous product of a fuel, such as propane or butane, for example, as disclosed in SAE Paper 790143.

These three types of apparatus, however, have the following drawbacks, respectively:

(1) Although the apparatus which employs the exhaust gas of an engine is more accurate than the other two types, it is difficult to accurately establish the desired conditions for evaluation, such as an excess air ratio (fuel-air ratio) and temperature. It requires excessive time for evaluation and therefore it is expensive. (2) Although the use of a mixture of various kinds of pure gas makes it possible to establish an excess air ratio of high stability as compared with what can be achieved by the apparatus employing the exhaust gas of an engine or propane gas burner, a large amount of gas is required to attain a flow rate which is comparable to that of the exhaust gas of an internal combustion engine. It is difficult to accurately establish the temperature of the gas which is employed in a large quantity. The gas is expensive, as it is a mixture of various kinds of gases.

(3) This type of apparatus employs gas which is obtained as a combustion product when a mixture of combustible gas and air is burned by a burner, thus a gas heater is not required. Moreover, a large volume of gas can be obtained which makes it easy to achieve a high flow rate, therefore, it is used for a wide range of inspection purposes in various fields of industry. However, the combustion gas is a product of nearly perfect combustion and contains only a small amount of uncombusted matter, as opposed to the exhaust gas of the internal combustion engine of an automobile. Therefore, it is often the case that the characteristics of a sensor which are determined by the burner apparatus differ from those which are obtained when the sensor is actually used with an internal combustion engine.

SUMMARY OF THE INVENTION

It is an object of this invention to provide an apparatus which can overcome the drawbacks of the prior art as hereinabove pointed out and can evaluate an oxygen sensor quickly, accurately and economically under desired conditions by employing a combustion product containing an appropriate amount of uncombusted matter.

This object is attained by an apparatus essentially comprising:

a device for mixing a fuel and an oxygen-containing gas in an appropriate ratio to prepare a fuel mixture;

a burner connected to the mixing device for burning the fuel mixture to produce a gaseous combustion product;

a tubular member extending from the burner for supplying the combustion product;

a nozzle connected to the tubular member for introducing a fuel and an oxygen-containing gas into the tubular member so that the combustion product may have a desired excess air ratio; and a mounting device of said sensor to be evaluated, the mounting device being disposed on said tubular member at a point downstream of said nozzle.

The apparatus of this invention is applicable to various types of oxygen sensors. They include a sensor of the type which employs an oxygen-ion conductive solid electrolyte, such as zirconia, and which detects a difference in partial pressure of the oxygen gas between the opposite sides of the electrolyte to determine the amount of oxygen gas that is in a particular environment, a sensor of the type which employs a semiconductor, such as titania, having an electrical conductivity varying with the partial pressure of the surrounding oxygen gas, and a sensor of the type which employs a combination of an oxygen pumping element and an oxygen gas detecting element.

Any combustible gas can be used as the fuel. It is, however, preferable to use propane, butane, or any other gas that is easy to transport. Moreover, it is also possible to use CO, $H_2$, etc. as the fuel which is introduced into the tubular member downstream of the burner.

Oxygen gas or air can be used as the oxygen-containing gas. The use of air is preferred for safety and economy.

The device which is connected to the tubular member downstream of the burner can be so connected thereto as to introduce a mixture of a fuel and an oxygen-containing gas thereinto not only at a single point, but also at a plurality of points. In the latter case, it is possible to introduce different gases at various locations, for example, a mixture of a fuel and an oxygen-containing gas at one point and only an oxygen-containing gas at another.

The combustive product must have a flow rate of at least 5m/sec. to ensure accurate evaluation of an oxygen sensor.

The gaseous mixture which is introduced into the tubular member downstream of the burner without being burned combines with the combustion product of the burner to produce in the evaluating chamber, an appropriately controlled atmosphere which still contains a certain proportion of uncombusted matter and is, therefore, similar in composition to the exhaust gas of an internal combustion engine. Therefore, the apparatus of this invention can determine the performance of an oxygen sensor accurately.

The ratio of the fuel and the oxygen-containing gas which are supplied to the burner and the ratio of the fuel and the oxygen-containing gas which are introduced downstream of the burner can both be varied easily and independently of each other.

Therefore, it is easy to produce in the evaluating chamber, an atmosphere which is very similar in composition to the exhaust gas of any of various types of internal combustion engines operating under any of various conditions. This makes it possible to accurately control the excess air ratio of the atmosphere, the proportion of uncombusted matter which it contains, the temperature of the atmosphere, and other conditions.

Moreover, the apparatus of this invention can evaluate an oxygen sensor at minimal cost due to the fact that it employs a gas of low cost as the fuel.

DETAILED DESCRIPTION OF THE INVENTION

Figure 1:
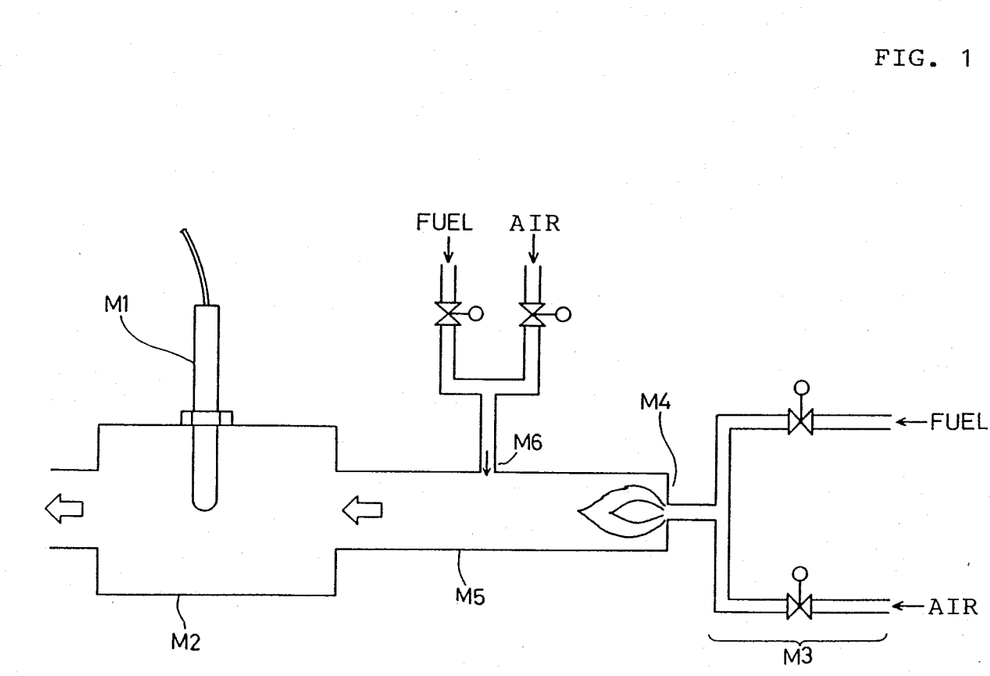
FIG. 1 is a diagram showing the principle of this invention.

Referring first to FIG. 1, an apparatus according to this invention comprises a housing defining an evaluating chamber M2 in which an oxygen sensor M1 is positioned, a device M3 for mixing a fuel and an oxygen-containing gas in an appropriate ratio to prepare a fuel mixture, a burner M4 connected to the mixing device M3 for burning the fuel mixture to produce a gaseous combustion product, a tubular member M5 extending from the burner M4 to the evaluating chamber M2 for supplying the combustible product into the chamber M2, and a device M6 connected to the tubular member M5 between the burner and the evaluating chamber for introducing a fuel and an oxygen-containing gas into the tubular member M5 so that the combustible product may have an appropriate excess air ratio when it is supplied into the evaluating chamber M2.

The evaluating chamber M2 may or may not form an integral part of the tubular member M5. The mixing device M3 may, for example, comprise a valve for regulating the amount of the fuel which is supplied, and a valve for regulating the amount of the oxygen-containing gas. The introducing device M6 may also be provided with a fuel valve and a valve for the oxygen-containing gas. The ratio of the fuel and oxygen-containing gas which are introduced through the device M6 can be varied independently of the ratio of the fuel and gas which are mixed by the device M3.

Figure 2:
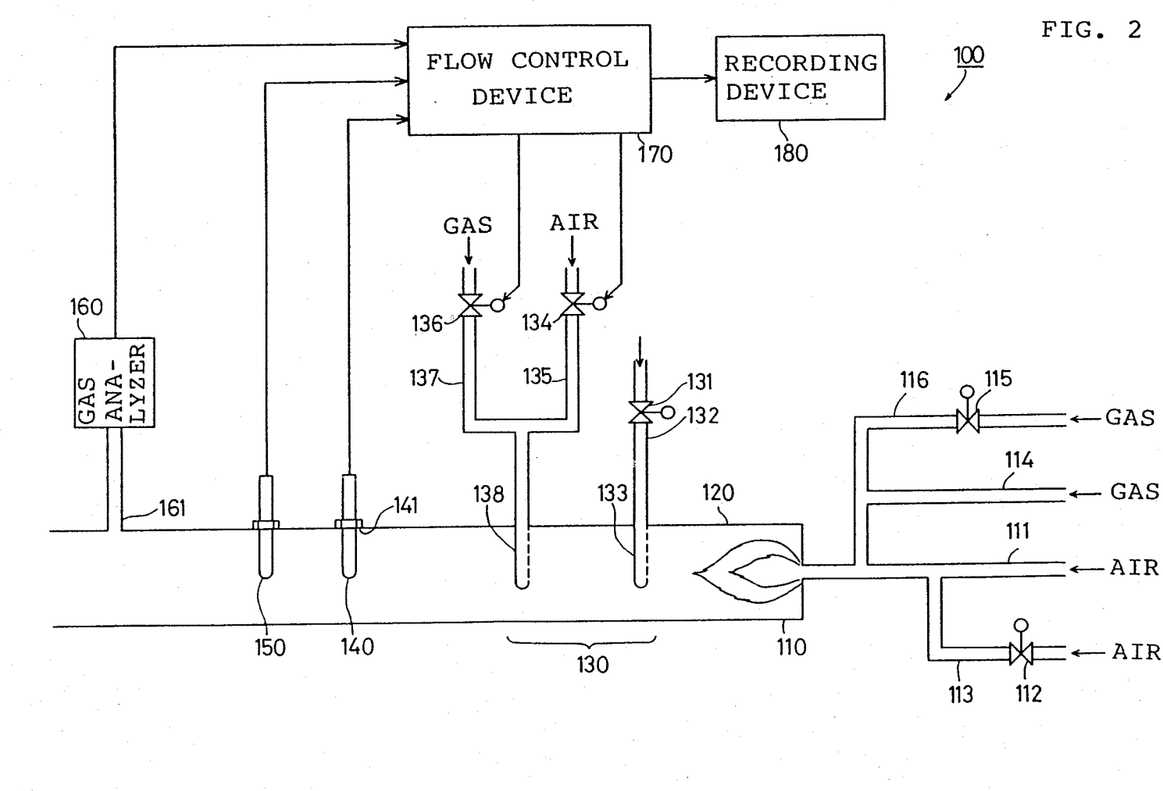
FIG. 2 is a diagrammatic representation of the essential features of an apparatus embodying this invention.

Referring to FIG. 2, there is diagramatically shown an apparatus 100 according to this invention. It comprises a burner 110 which enables the control of a variable excess air ratio, a combustion tube 120 having one end at which the burner 110 is provided, and defining both a tubular member for conducting the combustion product of the burner 110 and an evaluating chamber, an introducing device 130 provided on the combustion tube 120 downstream of the burner 110 for introducing an appropriate mixture of gas and air into the combustion tube 120, a device 141 provided downstream of the introducing device 130 for mounting a sensor 140 to be tested in the combustion tube 120, a standard oxygen sensor 150 provided downstream of the mounting device 141, and a gas sampling device 161 provided downstream of the standard oxygen sensor 150 and connected to a gas analyzer 160.

A main air supply tube 111, an auxiliary air supply tube 113, a main gas supply tube 114 and an auxiliary gas supply tube 116 are connected to the burner 110. The auxiliary air supply tube 113 is provided with a valve 112, and the auxiliary gas supply tube 116 is provided with a valve 115. Air is supplied from a compressor (not shown) to the air supply tubes 111 and 113, while propane gas is supplied from a gas bottle (not shown) to the gas supply tubes 114 and 116.

The introducing device 130 comprises a nozzle 133 connected to an air supply tube 132 having a valve 131, and a nozzle 130 to which an air supply tube 135 having a solenoid valve 134 and a gas supply tube 137 having a solenoid valve 136 are connected. Air is supplied from the compressor to the air supply tubes 132 and 135, while propane gas is supplied to the gas supply tube 137.

The signals from the sensors 140 and 150 and the output signal of the gas analyzer 160 are processed by a flow control device 170. The flow control device 170 controls the amounts of gas and air which are introduced into the combustion tube 120, and outputs the results of its processing to a recording device 180.

The sensor 140 causes feedback control of the control device 170 so that the atmosphere surrounding the sensor 140 has an excess air ratio which is equal to 1 at a theoretical air-fuel ratio $\lambda=1$, $\lambda=1$ corresponding to 450-500 mV output of the sensor 140. The excess air ratio obtained by any such feedback control or the output of the standard sensor 150 against the sensor 140 is utilized to determine the characteristics of the sensor 140. The excess air ratio is equal to the ratio of the amount of the air which is supplied for burning the fuel, and the fuel. When $\lambda=1$ (i.e. when the mixture is of the theoretical air-fuel ratio), the fuel is perfectly burned. If λ is larger than 1, the mixture is lean gas containing an excess of air, and if 2 is smaller than 1, it is rich gas having a shortage of air and its combustion leaves uncombusted matter.

The output voltage of a normal oxygen sensor is 200 mV at the highest if the atmosphere surrounding it is a lean gas, and is at least 700 mV if it is a rich gas. If the output of the sensor exceeds a voltage of 450 to 500 mV, the atmosphere surrounding it is a rich gas and if it is lower than a voltage of 450 to 500 mV, it is a lean gas. Therefore, the atmosphere may be of a theoretical air-fuel ratio $\lambda = 1$ by causing the control device 170 to control the solenoid valves 134 and 136 in accordance with the output of the sensor 140 in such a way that in the former case, a smaller amount of gas and a larger amount of air are supplied to the nozzle 138, while a larger amount of gas and a smaller amount of air are supplied thereto in the latter case.

However, if the output characteristics of the sensor 140 differ from what has hereinabove been described, the excess air ratio of the atmosphere under a feedback control which surrounds the sensor 140 does not show a theoretical excess air ratio.

A plurality of oxygen sensors 140 formed from titania and having different output characteristics were, therefore, tested one after another. The excess air ratio of the combustible product which has been formed by the feedback control of each sensor 140 was determined as the output of the gas analyzer 160 or the standard sensor 150. Every sensor 140 was of the type containing the same additive and having an equally shaped protector.

The output characteristics of each sensor 140 were accurately determined by positioning the sensors 140 in the exhaust gas of an engine, as stated above at (1). These characteristics and the results of evaluation by the apparatus 100 were compared for evaluating the apparatus. The tests described below were conducted by mounting the sensor to the internal combustion engine of the automobile, effecting feedback control of the engine in accordance with the output signal of the sensor and determining the excess air ratio of the controlled engine as the output characteristics of the sensor.

Prior to feedback control by the sensor 140, the valves 112 and 115 were adjusted such that the mixture of air and propane gas supplied to the burner 110 were of a ratio of 0.9, and the valve 131 was adjusted to control the amount of air through the nozzle 133 so that the combustion product of the burner 110 was of a ratio of 0.95.

The solenoid valves 134 and 136 were adjusted by the control device 170 in accordance with the output of the sensor 140 to vary the excess air ratio and amount of the mixture of air and propane gas supplied through the nozzle 138 so that the combustion product was of an excess air ratio varying in the range of 0.90 to 1.05.

TEST 1-1

Figure 3:
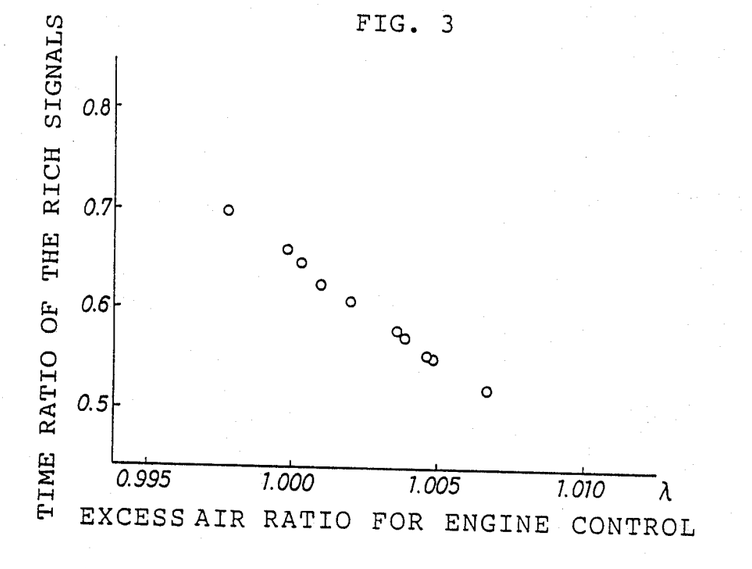
FIG. 3 is a graph showing the output characteristics of a sensor tested by an apparatus according to this invention (excess air ratio for engine control) in relation to the ratio of a "rich" signal.

FIG. 3 is a graph showing the output characteristics of the sensors 140 which were tested (excess air ratio as obtained by an engine control) in relation to the ratio of the time of the "rich" signal as indicated by the standard sensor 150 to the total measuring time (hereinafter referred to as the ratio of the "rich" signals) when the apparatus embodying this invention was controlled by the sensors 140. The "rich" signal of the standard sensor 150 is output by the control device 170 when the output of the standard sensor 150 exceeded a voltage of 450 to 500 mV. As is obvious from FIG. 3, the apparatus 100 embodying this invention showed a very high correlation between the ratio of the time for which the "rich" signal of the standard sensor 150 was output, to the testing time and the output characteristics of the sensor 140. The ratio of the "rich" signal, therefore, enabled the evaluation of the characteristics of the sensor 140 for the control of an internal combustion engine.

Figure 4:
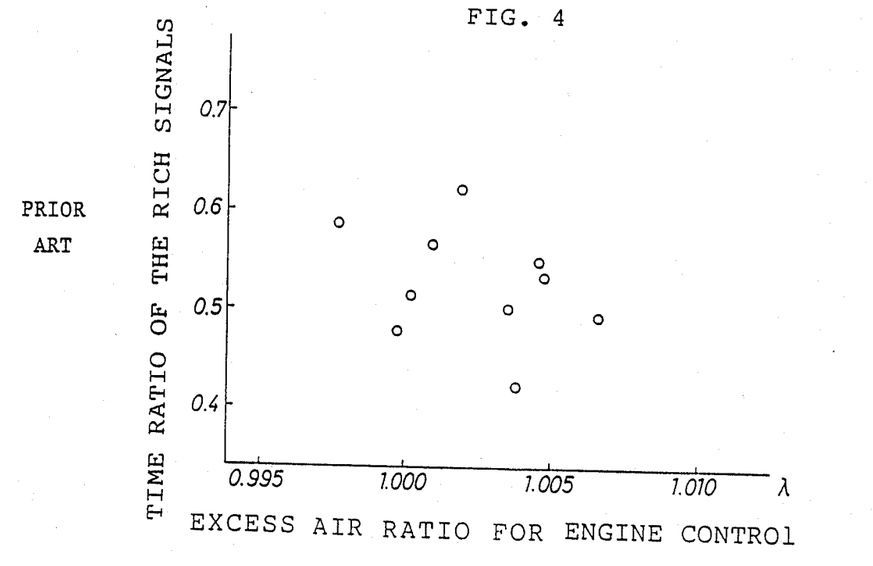
FIG. 4 is a graph showing the output characteristics of a sensor tested by a conventional apparatus in relation to the ratio of a "rich" signal.

FIG. 4 is a graph similar to FIG. 3, but showing the results obtained when a conventional apparatus employing a burner as stated at (3) above was controlled by the sensors. The apparatus was of the same construction as the apparatus according to this invention except that it did not include the introducing device 130, but that only the amounts of gas and air to be supplied to the burner 110 were controlled for the feedback control of the ratio of the combustion product. As is obvious from FIG. 4, the conventional apparatus hardly showed any correlation between the ratio of the time for which the "rich" signal of the standard sensor was output, to the testing time and the output characteristics of the sensor which was tested. By considering the time ratio of the "rich" signal, the conventional apparatus employing a burner could, therefore, not be used for evaluating the characteristics of the sensor for the control of an internal combustion engine.

TEST 1-2

Figure 5:
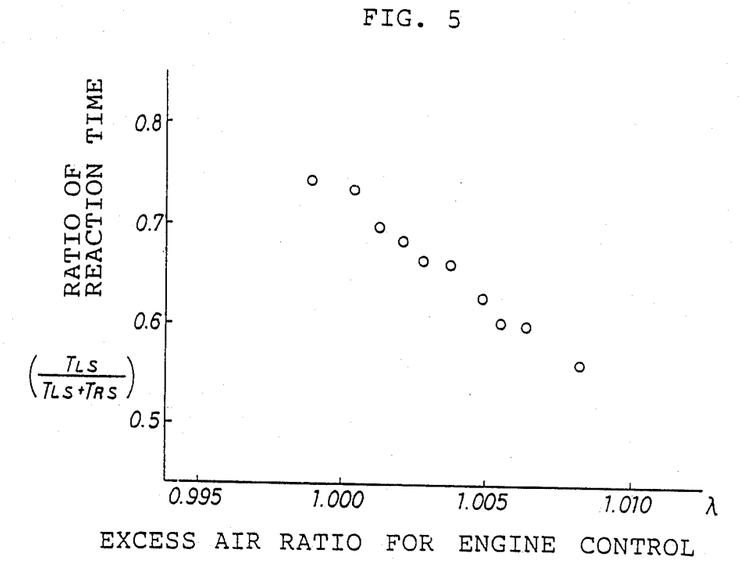
FIG. 5 is a graph showing the output characteristics of the sensor tested by an apparatus according to this invention in relation to the ratio of reaction time.

FIG. 5 is a graph showing the output characteristics (λ) of the sensors 140 in relation to the ratio of reaction time of the sensor 140 which was determined as described below. The combustion product of the apparatus 100 embodying this invention and carrying the sensor 140 to be tested was alternately changed between a rich gas having a ratio λ of 0.90 and a lean gas having a ratio of 1.05. This change was effected by changing the composition of the fuel mixture introduced through the device 130 by a timer provided in the control device 170. Measurement was made of the time required for the sensor 140 to output a standard voltage of 450 to 500 mV after each change has been effected. The ratio of the reaction time is expressed as:

$$T_{RS}/(T_{RS}+T_{LS})$$

where "$T_{RS}$" represents the length of time required for the sensor to output the standard voltage after the combustion product had been changed to a rich gas mixture and "$T_{LS}$" represents the length of time required for the sensor to output the standard voltage after the combustion product had been changed to a lean gas mixture. As is obvious from FIG. 5, the apparatus 100 of this invention showed a very high correlation between the ratio of the reaction time of the sensor 140 and its output characteristics (λ). The ratio of reaction time, therefore, enabled the evaluation of the characteristics of the sensor 140 for the control of an internal combustion engine. In other words, the apparatus of this invention corresponds rapidly to the change from a rich gas mixture to a lean gas mixture and vice versa.

Figure 6:
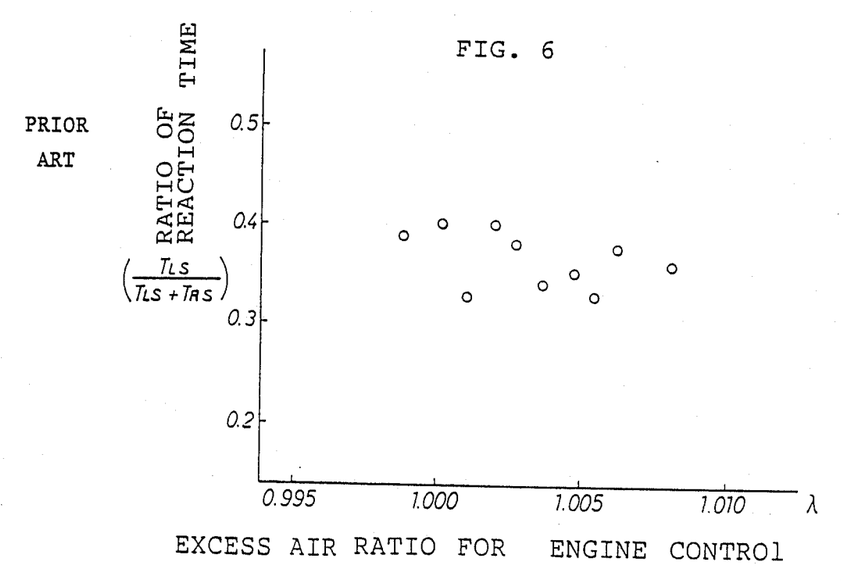
FIG. 6 is a graph similar to FIG. 5, but showing the results obtained by employing a conventional apparatus.

FIG. 6 is a graph similar to FIG. 5, but showing the results obtained when a conventional apparatus employing a burner as stated at (3) was controlled by the sensor. As is obvious from FIG. 6, the conventional apparatus hardly showed any correlation between the ratio of reaction time of the sensor and its output characteristics (λ). By considering the ratio of the reaction time, the conventional apparatus employing a burner could, therefore, not be used to evaluate the characteristics of the sensor for the control of the internal combustion engine.

TEST 1-3

Figure 7:
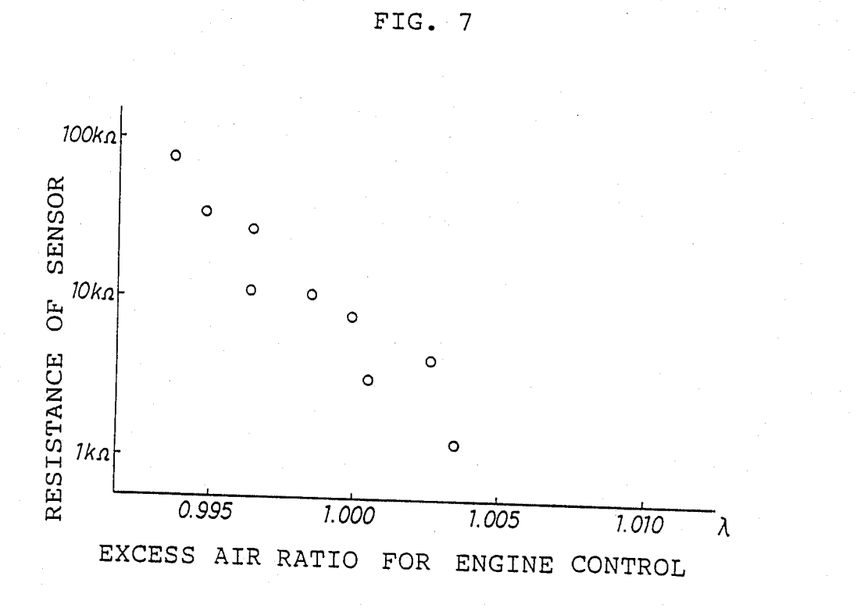
FIG. 7 is a graph showing the output characteristics of a sensor tested by an apparatus according to this invention in relation to its resistance.

FIG. 7 is a graph showing the output characteristics ($\lambda$) of the sensors 140 in relation to their resistance when the combustion product had a ratio $\lambda$ of 0.90. This resistance was determined as set forth below. The valves 112 and 115 were controlled so that the combustion product of the burner 110 has a ratio of 1.02, and propane gas was introduced through the nozzle 138 until the combustion product has a ratio $\lambda$ of 0.90. When it had a ratio $\lambda$ of 0.90, the resistance of the sensor 140 was measured. As is obvious from FIG. 7, the apparatus 100 of this invention showed a very high correlation between the resistance which the sensor 140 showed when the combustion product had a ratio $\lambda$ of 0.90 and the output characteristics ($\lambda$) thereof. The resistance, therefore, made it possible to evaluate the characteristics of the sensor 140 for the control of the internal combustion engine.

Figure 8:
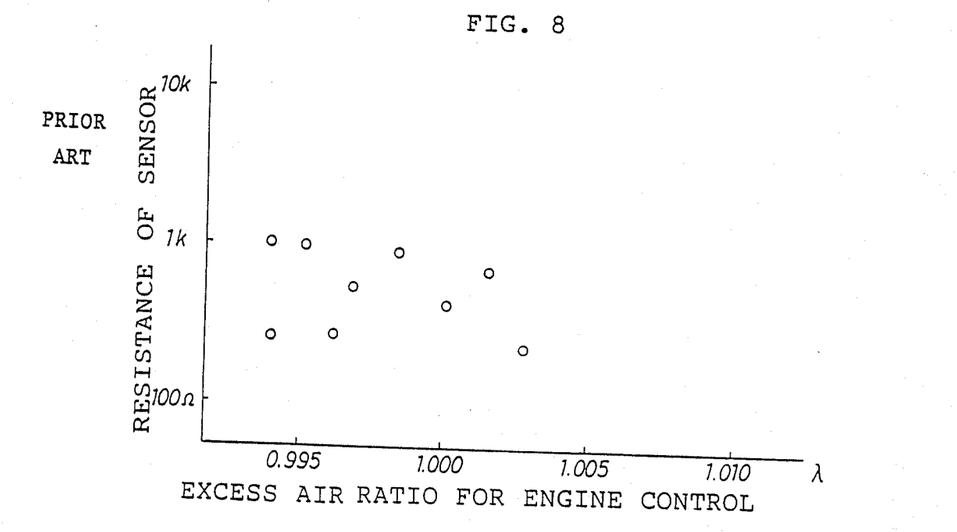
FIG. 8 is a graph similar to FIG. 7, but showing the results obtained by employing a conventional apparatus.

FIG. 8 is a graph similar to FIG. 7, but showing the results obtained when a conventional apparatus employing a burner was used. The resistance of the sensor was measured when the combustion product of the burner had a ratio of 0.90, as the ratio of the atmosphere in the vicinity of the sensor was equal to that of the combustion product of the burner. As is obvious from FIG. 8, the apparatus hardly showed any correlation between the resistance which the sensor showed when the combustion product had a ratio of 0.90 and the output characteristics ($\lambda$) thereof. Therefore, the conventional apparatus employing a burner could not be used to evaluate the characteristics of the sensor for the control of the internal combustion engine.

TEST 1-4

Figure 9:
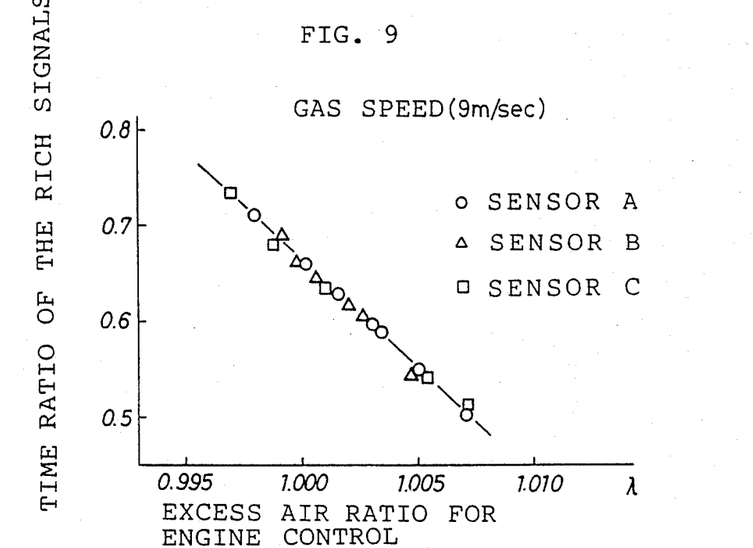
FIG. 9 is a graph showing the output characteristics of sensors tested by an apparatus according to this invention at a flow rate of 9 m/sec. in relation to the ratio of a "rich" signal.
Figure 10:
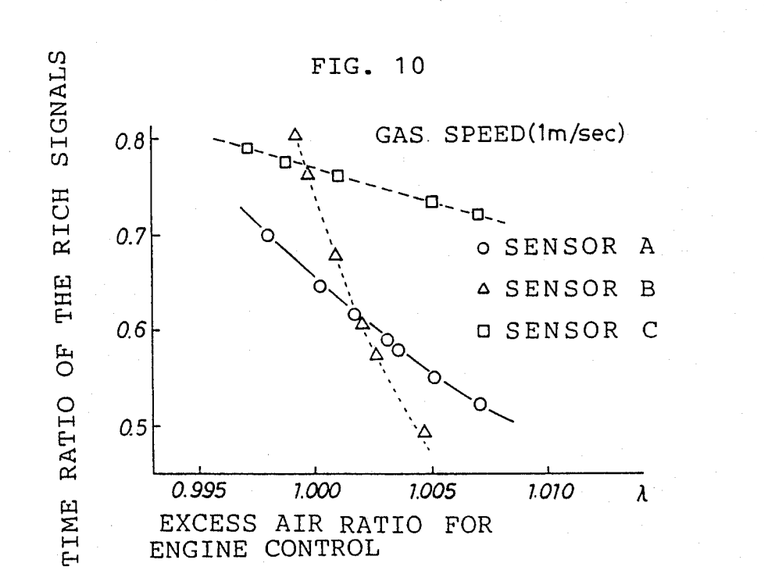
FIG. 10 is a graph similar to FIG. 9, but showing the results obtained at a flow rate of 1 m/sec.

FIGS. 9 and 10 are graphs showing the relation between the output characteristics ($\lambda$) of the sensors 140 and the time ratio of the "rich" signals which were indicated by the standard sensor 150 when the apparatus of this invention was controlled by the sensors 140. FIG. 9 shows the results which were obtained when the combustable product had a flow rate of 9 m/sec., while FIG. 10 shows the results obtained when it has a flow rate of 1 m/sec. This test was conducted by using three types of sensors 140, as opposed to TESTS 1 to 3. Type A and B sensors were both formed from titania and were of the same shape, but contained different additives. Type C sensors contained the same additive as that which type A sensors contained, but their protectors has a different shape.

In FIGS. 9 and 10, each circle, triangle and square denote type A, B and C sensors, respectively. The procedure of TEST 1 was repeated for determining the ratio of the "rich" signals which had been output by the standard sensor 150. As is obvious from FIGS. 9 and 10, the apparatus 100 of this invention showed a high correlation between the ratio of the time for which the "rich" signals were output by the standard sensor 150, to the testing time and the output characteristics ($\lambda$) of the sensors 140, irrespective of the flow rate of the combustion product, if the sensors were of the same type. Therefore, the ratio of the "rich" signals could be used to evaluate the characteristics of the sensors 140 for the control of an internal combustion engine. Their correlation was very high irrespective of the type of the sensors 140 when the combustion product had a high flow rate, as is obvious from FIG. 9. Results similar to those shown in FIG. 9 were obtained when the combustion product has a flow rate of at least 5 m/sec.

Figure 11:
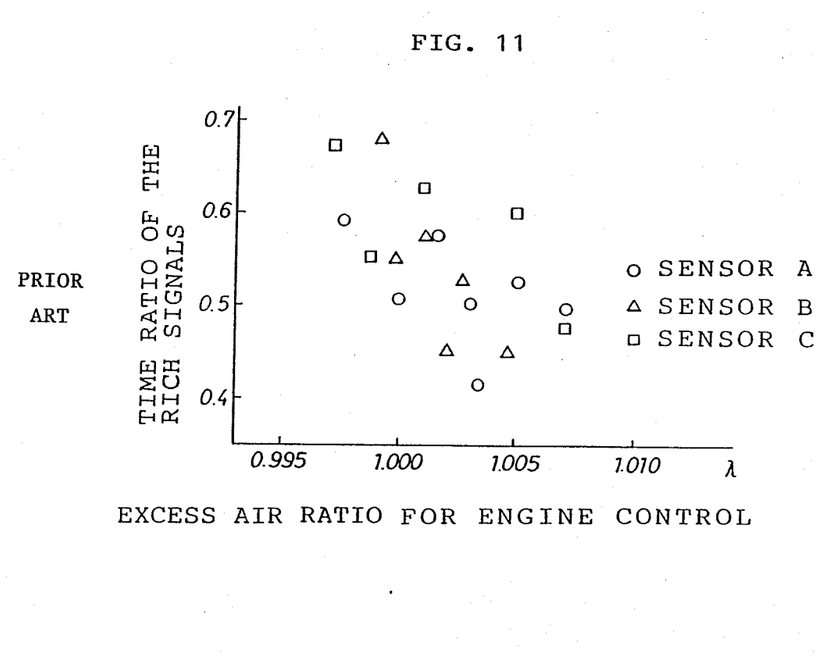
FIG. 11 is a graph showing the output characteristics of sensors tested by employing a conventional apparatus in relation to the ratio of a "rich" signal.

FIG. 11 is a graph similar to FIG. 9 or 10, but showing the results which were obtained when the conventional apparatus including a burner was employed. As is obvious therefrom, the conventional apparatus hardly showed any correlation between the ratio of the time for which the "rich" signals were output by the standard sensor, to the testing time and the output characteristics ($\lambda$) of the sensors, even when sensors of the same type were compared. Therefore, by considering the time ratio of the "rich" signals the conventional apparatus employing a burner could not be used to evaluate the sensors for the control of an internal combustion engine.

The results of TESTS 1 to 4 comfirmed that the apparatus 100 of this invention can be used to evaluate oxygen sensors accurately. Although the foregoing results were obtained by comparing the output characteristics of the sensors 140, which had been previously determined, with the ratio of the output of the standard sensor, the ratio of reaction time, or the resistance of the sensors, similar results were obtained when the excess air ratio obtained from analysis by the gas analyzer 160 of the combustion product of the apparatus 100 controlled by the sensor 140, or the excess air ratio obtained by an air-fuel ratio sensor provided on the combustion tube 120 was employed instead of the output characteristics of the sensor 140.

Figure 12:
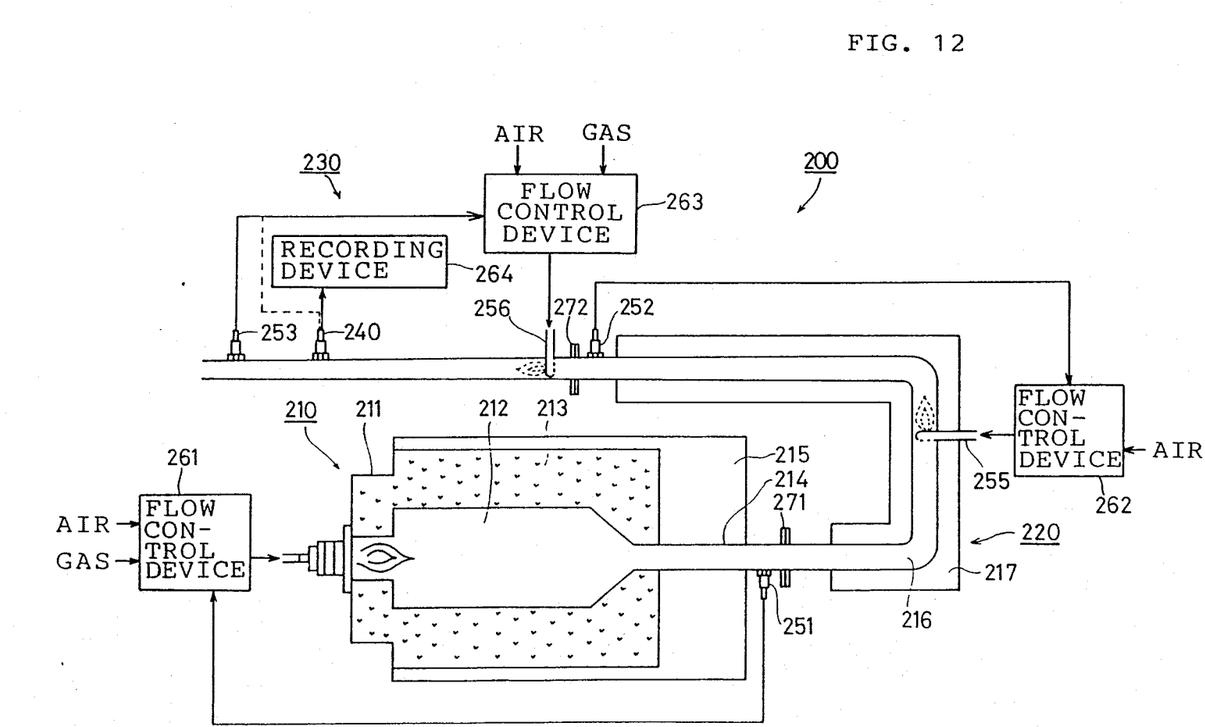
FIG. 12 is a diagram showing a modified form of an apparatus according to this invention.

FIG. 12 shows an explanatory illustration showing the construction of another apparatus for evaluating an oxygen sensor according to the present invention. This apparatus 200 is mainly composed of an exhaust gas generator 210 generating exhaust gas including CO, etc., an offsetting portion 220 allowing a basis excess air ratio including CO, $O_2$ by adding air to the exhaust gas, and a rich/lean setting portion 230 which forms an excess air condition by adding gas or air to the exhaust gas having the basis excess air ratio (hereafter called "lean") or forms an excess fuel ratio (hereafter called "rich"). An oxygen-gas sensor 240 to be evaluated is exposed to a combustion tube 216 adjusted at the rich/lean setting portion 230. The combustion tube 216 is connected by a flange 272.

The exhaust gas generator 210 generates the exhaust gas which contains enough flow volume and appropriate temperature for evaluating the sensor 240. The excess air ratio of this exhaust gas is set to $\lambda=0.95$ for example. The offsetting portion 220 functions to compensate the excess air ratio to $\lambda=1.0$ for example by adding air to this exhaust gas. The exhaust gas compensated in this offsetting portion 220 contains both lean components such as $O_2$ and rich components such as CO simultaneously which are of generally the same composition as those present in the exhaust gas of an internal combustion engine.

The rich/lean setting portion 230 functions to change the exhaust gas thus compensated to a rich phase by adding fuel to a value (for example $\lambda=0.95$) or a lean phase by adding air to a value (for example $\lambda=1.05$) respectively based on the excess air ratio (1.0) set at the offsetting part 220. By exposing the sensor 240 to be evaluated to the exhaust gas in this manner, the sensor 240 is placed under the same conditions as it is subjected to in a car.

The construction of the offsetting portion 220 is explained as follows. First, the fuel exhaust gas generator 210 is explained. The fuel exhaust gas generator 210 is provided with propane gas (hereaftr called "gas") as a fuel supplied from a fuel tank (not shown), a flow control device 261 to mix air supplied from a compressor not shown, a burner 211 for burning this mixed air to generate the exhaust gas and a A/F sensor 251 fixed on a combustion tube 214 downstream of the burner 211.

The aforesaid flow control device 261 serves to adjust the mixture ratio of air or gas so that the excess air ratio detected by the A/F sensor 251 coincides with the excess air ratio ($\lambda=0.95$) for example which has already been predetermined. This adjustment is performed by regulating the opening degree of a mass flow regulator (not shown) which consists of the flow control devide 261 equipped with a thermostatic valve (not shown). The combustion chamber 212 of the burner 211 is formed of an adiabatic material 213. The combustion tube 214 is cooled by a water-cooled jacket 215 and connected to combustion tube 216 by a flange 271.

The A/F sensor 251 may be a sensor combining an oxygen pump element using oxygen ionized solid electroliquid material such as zirconia for example, with an oxygen battery element. This A/F sensor 251 can measure the excess air ratio from lean phase ($\lambda>1$) to rich phase ($\lambda<1$).

Next, the offsetting portion 220 is explained. The offsetting portion 220 is provided with a nozzle 255 adding air to the exhaust gas from the exhaust gas generating part 210, a flow control device 262 adjusting air quantity supplied to this nozzle 255, and an A/F sensor 252 fixed on the downstream end of the nozzle 255.

The flow control device 262 functions to adjust air quantity in the same manner as the flow control device 261 so that the excess air ratio detected by A/F sensor 252 is coincided with the pre-determined excess air ratio ($\lambda=1.0$ for example). The combustion tube 216 is water cooled covered by the water-cooled jacket 217. Through this tube, the exhaust gas is set to nearly the same temperature as that of exhaust gas from the car. The A/F sensor 252 used is the same type as the A/F sensor 251.

Further, the rich/lean setting portion 230 is explained. The rich/lean setting portion 230 is provided with a nozzle 256 for adding gas or air to the exhaust gas adjusted at the offsetting portion 220, a flow control device 263 adjusting air quantity or fuel gas quantity supplied to this nozzle, and an A/F sensor 253 fixed on the downstream end of the nozzle 256.

The flow control device 263 functions in the same manner as the flow control device 261 to add air or fuel gas so that the excess air ratio of the fuel exhaust gas detected by the A/F sensor 253 coincides with the pre-determined excess air ratio ($\lambda=1.05$ or $\lambda=0.95$ for example). Moreover, the A/F sensor 253 used is the same type as the A/F sensor 251. On the other hand, the flow control device 263 may be controlled by using the sensor 240 to be evaluated depending on a value of the sensor 240 shown by the dotted line in FIG. 12.

The output of sensor 240 to be evaluated is recorded in a recording device 264. For precise flow regulation, the A/F sensors 251, 252, 253 are correlated as required by using standard gas (a gas of which the air/fuel ratio is predetermined). Moreover, when required, it is possible to equip a standard A/F sensor or gas analyzer measuring the excess air ratio of the fuel exhaust gas to which the sensor to be evaluated 240 is exposed, near to or downstream thereof. Further, controlling the flow control devices 261, 262, 263 and recording the output of sensor 240 to be evaluated can be undertaken all by one electronic control unit.

TEST 2-1

The excess air ratio of the exhaust gas generator 210 and the offsetting portion 220 are as shown in the table below, wherein the excess air ratio of rich/lean setting portion 230 in changed between rich and lean phases shown in table below in 0.5 seconds intervals by using a timer (not shown). The gas components of exhaust gas emitted from respective portions are also shown in the TABLE.

|  |  |  | GAS COMPOSITION |
|---|---|---|---|
| BURNER PORTION |  | 0.95 | $CO, CO_2, H_2O, N_2$ |
| OFFSET PORTION |  | 1.0 | $CO, O_2, CO_2, H_2O, N_2$ |
| RICH | LEAN | 1.05 | $CO, O_2, CO_2, H_2O, N_2$ |
| LEAN SETTING PORTION | RICH | 0.95 | $CO, C_3H_8, O_2, CO_2, H_2O, N_2$ |

Measuring the lapse of time "$T_{LS}$" from when the exhaust gas of the sensor 240 to be evaluated is changed to lean, to the time when it reaches standard voltage (450–500 mV) and the lapse of time "$T_{RS}$" from when the fuel exhaust gas is changed to rich, to when it reached the standard voltage, the sensor 240 to be evaluated is evaluated depending on the time ratio $T_{RS}/(T_{RS}+T_{LS})$ obtained by the reaction of sensor 240.

Figure 13:
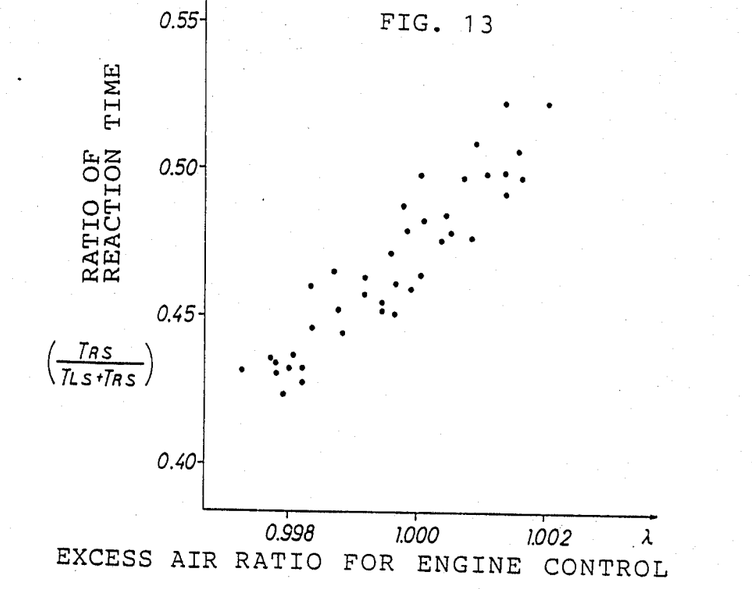
FIG. 13 is a graph showing the output characteristics of sensors tested by an apparatus according to a second embodiment of this invention in relation to the ratio of reaction time.

FIG. 13 is a diagram showing the relationship between the excess air ratio for engine control and the ratio of reaction times as for various types of sensors to be evaluated.

In the preferred embodiment of the present invention, the apparatus 200 for evaluating the oxygen sensor is evaluated by comparing the detected characteristic values of the sensor 240 pre-measured precisely in the conventional method 1 where the sensor is inserted into the exhaust gas previously described with the values measured according to the present evaluation method.

The sensor to be evaluated is mounted on a car and the engine is feed-back controlled by the output of the sensor. In so doing, the detected characteristic values are expressed in the excess air ratio for engine control in this manner. As shown clearly in FIG. 13, there is a sharp correlation between the ratio of reaction time of the sensor 240 and detected characteristics (excess ratio for engine control) of sensor 240. Accordingly, the apparatus 200 of the present invention proved to be quite instrumental in evaluating the oxygen sensor with high precision.

Figure 14:
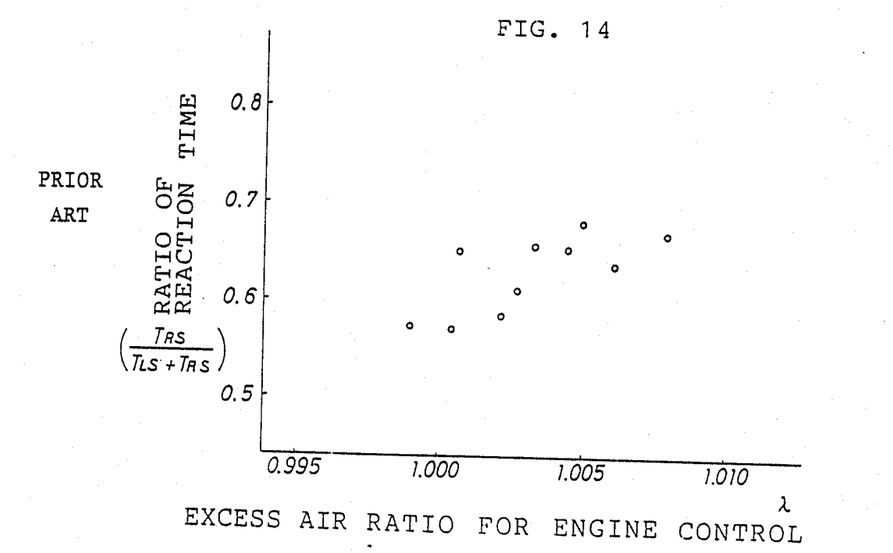
FIG. 14 is a graph similar to FIG. 13, but showing the results obtained by employing a conventional apparatus.

For comparison, FIG. 14. shows a relationship between the ratio of the reaction time and the excess air ratio for an engine control and for a conventional burner type apparatus (prior art) for evaluating oxygen sensor. As shown in FIG. 14, there is not much correlation as is appreciably approved with the significant tangential rise along coordinate axis though there is some correlation between the ratio of reaction time and excess air ratio for engine control when the conventional burner type apparatus for evaluating the oxygen sensor is used.

Judging from the ratio of reaction time, this conventional burner type apparatus for evaluating the oxygen sensor proves to be unable to evaluate the characteristics of the sensor.

TEST 2-2

First, the excess air ratio of exhaust gas generator 210 and the offsetting portion 220 are set in the same manner as in the above evaluation method 1. Second, the rich-/lean setting portion 230 is feed-back controlled to gain $\lambda=1$ by using the sensor to be evaluated 240 of rich-/lean setting portion 230. Then, the excess air ratio (excess air ratio for controlling the apparatus) is obtained. Based on this value, the sensor 240 is evaluated. When the engine is feed-back controlled, the excess air ratio is measured by the A/F sensor 253 or separately installed gas analyzer (not shown).

Figure 15:
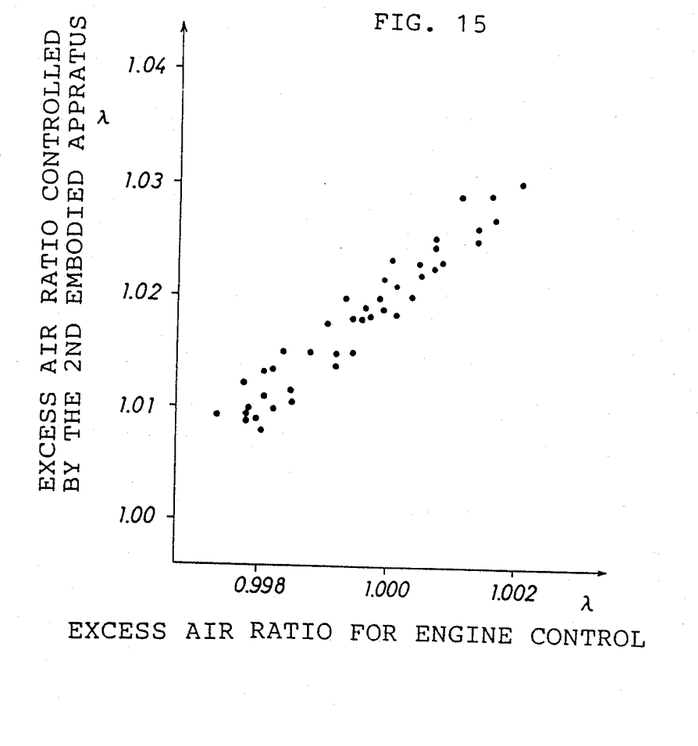
FIG. 15 is a graph showing the output characteristics of the sensors tested by a modified apparatus in relation to excess air ratio controlled by a second embodiment of this invention.

FIG. 15 is a diagram showing a relationship between the excess air ratio for engine control and the excess air ratio controlled by the apparatus 200 for various sensors 240 to be evaluated when the apparatus 200 for evaluating the oxygen sensor according to the present embodiment is used.

In this embodiment, comparing the detected characteristics of the sensor 240 to be evaluated which is precisely measured by the method where the sensor is inserted beforehand into the exhaust gas emitted from the previously described engine in the same manner as in the evaluation test 1 with measured values according to the present evaluation method, the apparatus 200 of the present invention for evaluating the oxygen sensor of the present embodiment is evaluated.

As shown in FIG. 15, there is a sharp correlation between the excess air ratio obtained when the apparatus 200 for evaluating the oxygen sensor is feed-back controlled by using the sensor 240 to be evaluated in the present evaluation method using the apparatus for evaluating the oxygen sensor of the present embodiment and the detected characteristics of the sensor 240. Accordingly, the sensor 240 evaluated by the apparatus 200 can evaluate the excess air ratio of an engine with high precision when it is mounted on an engine.

According to the evaluation method 2 as described above, the sensor 240 to be evaluated is evaluated using the excess air ratio controlled by tthe evaluation apparatus.

Instead of this excess air ratio being controlled by the apparatus, the ratio in which the A/F sensor 253 for measuring the excess air ratio generates a rich signal can be used when an engine is feed back controlled. This rich signal is a signal outputted when the output of A/F sensor exceeds the rated voltage (450–500 mV) as previously described.

Moreover, the apparatus 200 for evaluating the oxygen sensor can also evaluate the sensor 240 to be evaluated by using the resistance value of the sensor 240 at the excess air ratio of $\lambda=0.90$.

As so far explained, it has been confirmed that the apparatus for evaluating the oxygen sensor of the present invention can evaluate oxygen sensors in various ways. The apparatus for evaluating the oxygen sensor according to the present embodiment employs the evaluating manner in which engine feed back control is executed in exhaust gas generator 210, the offsetting portion 220 and rich/lean setting portion 230 respectively. Therefore, the excess air ratio of exhaust gas into which sensor 240 to be evaluated is inserted can be controlled with high precision.

In the apparatus for evaluating the oxygen sensor using the conventional burner for example, the excess air ratio was controlled with a precision of $\pm 0.01\lambda$ while the apparatus 200 for evaluating the oxygen sensor can be controlled with a precision below $\pm 0.001\lambda$ according to the present embodiment.

Further, lower priced gas may be used in this embodiment as compared with the oxygen gas evaluation in which the oxygen sensor is evaluated by using model gas or gas from an internal combustion engine. Thus, the oxygen sensor can be evaluated economically.

What is claimed is:

1. An apparatus for evaluating an oxygen sensor comprising:
    a mixing device for mixing a fuel and an oxygen-containing gas in an appropriate ratio to prepare a fuel mixture;
    a burner connected to said mixing device for burning said fuel mixture to produce a gaseous combustion product;
    a tubular member extending from said burner for supplying said combustion product;
    a nozzle connected to said tubular member downstream of said burner for introducing at least one of a fuel and an oxygen-containing gas into said tubular member so that an excess air ratio of said combustion product may be controlled; and
    a mounting device in which said sensor to be evaluated is disposed, said mounting device being positioned on said tubular member, at a point downstream of said nozzle.

2. An apparatus as claimed in claim 1, wherein said apparatus further comprises a flow control device for controlling the excess air ratio at said nozzle so that the excess air ratio substantially equals a desired excess air ratio.

3. An apparatus as claimed in claim 2, wherein said apparatus further comprises a standard oxygen sensor positioned adjacent said mounting device and on said tubular member, said standard oxygen sensor operating in cooperation with said flow control device to maintain said excess air ratio at said nozzle at the desired excess air ratio.

4. An apparatus as claimed in claim 2, wherein said apparatus further comprises a gas analyzer disposed downstream of said mounting device, said gas analyzer operating in cooperation with said flow control device to maintain said excess air ratio at a portion of said nozzle at the desired excess air ratio.

5. An apparatus as claimed in claim 1, said apparatus further comprising:
    a second nozzle for supplying air into said tubular member, said second nozzle being disposed on said tubular member between said burner and said nozzle;
    a second flow control device for maintaining an excess air ratio at said second nozzle at a predetermined value by sensing an excess air ratio downstream of said second nozzle; and
    a third flow control device for maintaining an excess air ratio of the mixture supplied to said burner at a predetermined excess air ratio.

6. An apparatus as claimed in claim 5, wherein said third flow control device includes an oxygen sensor on said tubular member, at an upstream portion of said second nozzle.

7. An apparatus as claimed in claim 5, wherein said second flow control device includes an oxygen sensor on said tubular member, between said nozzle and said second nozzle.

8. An apparatus for evaluating an oxygen sensor comprising:

a first mixing device for mixing a fuel and an oxygen-containing gas in an appropriate ratio to prepare a fuel mixture;

a burner connected to said mixing device for burning said fuel mixture to produce a gaseous combustion product;

a tubular member extending from said burner for supplying said combustion product;

a second mixing device connected to said tubular member for introducing at least one of a fuel and an oxygen-containing gas into said tubular member so that an excess air ratio of said combustion product may be controlled; and a mounting device in which said sensor to be evaluated is disposed, said mounting device being positioned on said tubular member, at a point downstream of said nozzle.

* * * * *

UNITED STATES PATENT AND TRADEMARK OFFICE
CERTIFICATE OF CORRECTION

PATENT NO. : 4,825,683
DATED : May 2, 1989
INVENTOR(S) : Akio TAKAMI, Ken MINOHA, Mineji NASU and Toshifumi SEKIYA It is certified that error appears in the above-identified patent and that said Letters Patent is hereby corrected as shown below:

In the specification, column 6, lines 42-44, "$T_{RS}/(T_{RS}+T_{LS})$" should read --$T_{LS}/(T_{LS}+T_{RS})$--.

Signed and Sealed this

Twenty-eighth Day of December, 1993

Attest:

BRUCE LEHMAN

*Attesting Officer*     *Commissioner of Patents and Trademarks*